United States Patent [19]

Deacon et al.

[11] Patent Number: 5,540,827
[45] Date of Patent: Jul. 30, 1996

[54] DIRECTIONAL FLOW ION-JUNCTION BRIDGE

[75] Inventors: Mark E. Deacon, Rochester; William F. Gottermeier, Pittsford, both of N.Y.

[73] Assignee: Johnson & Johnson Clinical Diagnostics, Inc., Rochester, N.Y.

[21] Appl. No.: 466,638

[22] Filed: Jun. 6, 1995

[51] Int. Cl.⁶ .................. G01N 27/333; G01N 27/401
[52] U.S. Cl. ............................ 204/416; 204/435
[58] Field of Search ..................... 204/435, 416, 204/418, 419

[56] References Cited

U.S. PATENT DOCUMENTS

| | | | |
|---|---|---|---|
| 4,053,381 | 10/1977 | Hamblen et al. | 204/416 |
| 4,273,639 | 6/1981 | Gottermeier | 204/416 |
| 4,437,970 | 3/1984 | Kitajima et al. | 204/435 |
| 4,556,474 | 12/1985 | Pierson | 204/416 |
| 5,147,524 | 9/1992 | Bradley | 204/435 |
| 5,346,606 | 9/1994 | Christner et al. | 204/435 |

OTHER PUBLICATIONS

Webster's Seventh New Collegiate Dictionary, 1963, month unavailable p. 1010.

*Primary Examiner*—T. Tung
*Attorney, Agent, or Firm*—Dana M. Schmidt

[57] ABSTRACT

An ion-junction fibrous bridge and a potentiometric test element incorporating the same, wherein the fibers extending generally along the center-line between two liquid access apertures in the bridge, are readily capable of conducting aqueous liquid through the bridge, and fibers extending at an angle of at least 20° from said center-line are not readily capable of conducting aqueous liquid.

10 Claims, 5 Drawing Sheets

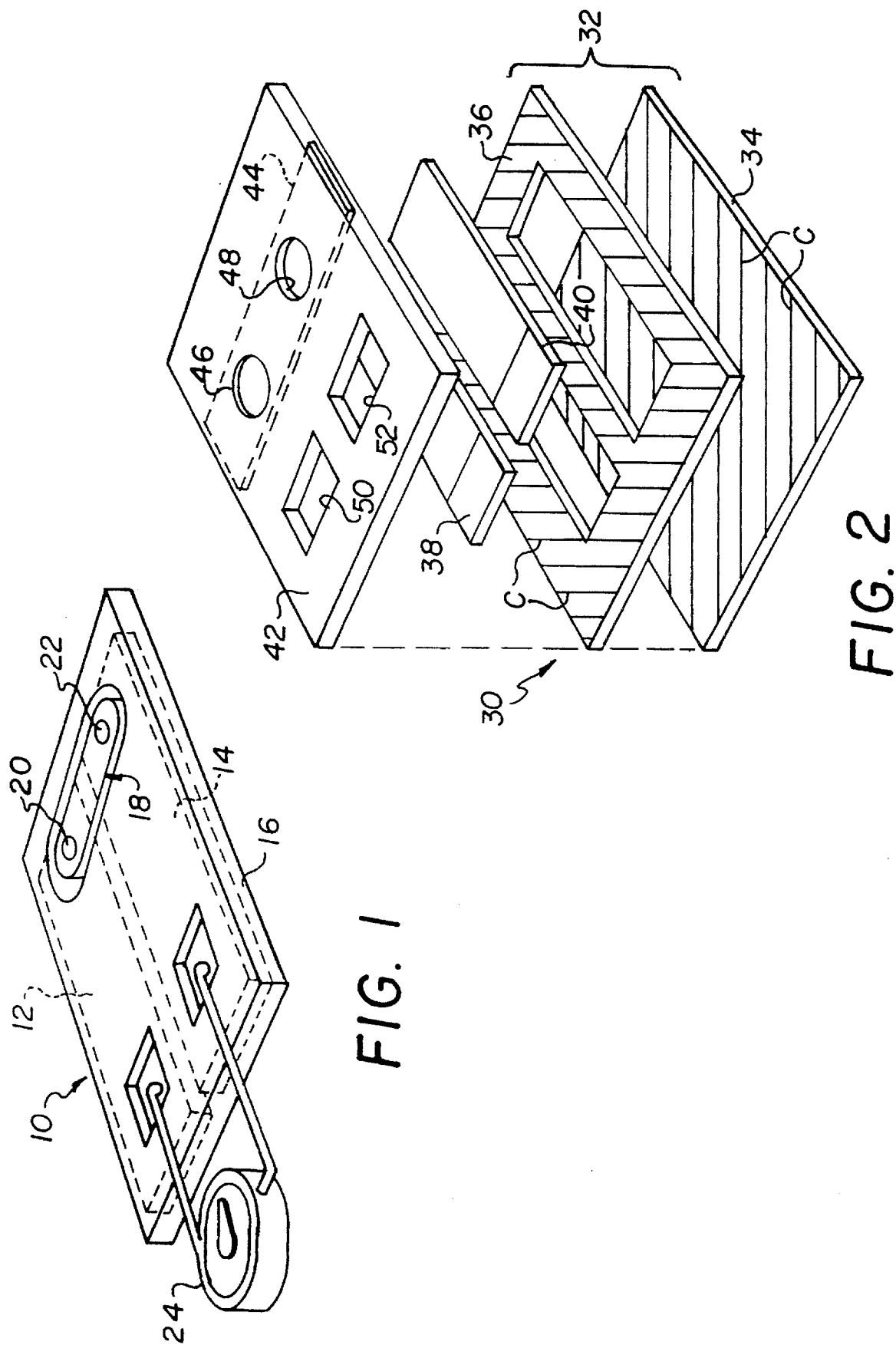

DIRECTIONAL FLOW ION-JUNCTION BRIDGE

FIELD OF THE INVENTION

This invention relates to an ion-junction bridge, and a potentiometric test element incorporating the same, for clinical diagnosis of an ionic analyte.

BACKGROUND OF THE INVENTION

In the field of clinical diagnosis, it is common to test certain ionic analytes using a potentiometric slide test element providing a differential potential between a reference liquid and the patient sample liquid, both of which are aqueous. Such an element features two substantially identical ion-selective electrodes held spaced apart in a frame, and an ion-junction bridge connecting them. The bridge is apertured so as to provide two liquid access apertures each aligned and in fluid contact with one of the electrodes. To ensure the two liquids will flow together within the bridge, the bridge is constructed to induce liquid flow away from the entrance aperture toward the other aperture. For example, the bridge can be a sheet of fibers, e.g., paper; on or embedded within the frame. An example of the first is shown in U.S. Pat. No. 4,053,381 and an example of the second is shown in U.S. Pat. No. 4,273,639.

Although such examples have worked admirably, they do have a minor disadvantage—liquid flow within the bridge tends to occur in all directions, rather than just from one aperture to the other. At best, this non-directional flow requires more than the minimum amount of liquid. At worst, liquid flowing in non-desired directions can lead to shorting.

As a result, mechanical means are preferably added to keep liquid flow from extending in the non-desired direction., namely, directions angled away from the straight-line direction between the apertures. An example of dams placed parallel to the straight-line direction to cut down on flow away from that direction, is shown in U.S. Pat. No. 4,556,474. Although such dams can reduce the amount of liquid required, they do further complicate the manufacturing process.

Thus, there has been a need, prior to the invention, for an ion-junction bridge that inherently favors flow directions that are only the desired flow directions, minimizing the volume of liquid needed.

SUMMARY OF THE INVENTION

We have constructed an ion-junction bridge, and a test element using the same, which solve the aforesaid need.

More specifically, there is provided, in accord with one aspect of the invention, an ion-junction bridge for bringing two liquids together to make an ion exchange junction, the bridge comprising a sheet of fibers having two apertures therethrough. The bridge is improved in that the fibers comprise a material which favors aqueous flow in no more than two generally orthogonal directions and suppresses aqueous flow in directions angled away from either of the orthogonal directions by more than about 20°, one of the orthogonal directions being generally aligned with the two apertures, so that aqueous liquids deposited in said apertures will flow primarily in the orthogonal directions.

In accord with another aspect of the invention, there is provided a potentiometric test element comprising a frame, two substantially identical ion-selective electrodes mounted spaced apart on the frame, and an ion-junction bridge extending between the electrodes, the bridge comprising a sheet of fibers having two liquid access apertures through the sheet, each aperture being disposed above and in fluid contact with one of the electrodes, the fibers comprising a material which favors aqueous flow no more than two generally orthogonal directions and suppresses aqueous flow in directions angled away from either of the orthogonal directions by more than about 20°, one of the orthogonal directions being generally aligned with the two apertures, so that aqueous liquids deposited in said apertures will flow primarily in the orthogonal directions.

Accordingly, it is an advantageous feature of the invention that an ion bridge for a test element inherently provides no more than orthogonally-directed flow, one of which is generally aligned with the two apertures, thereby reducing the amount of liquid needed to form the ion-junction needed to do the potentiometric test.

It is a related advantageous feature that such a bridge reduces the likelihood of liquid flow to areas of the bridge that can cause problems.

Other advantageous features will become apparent upon reference to the following Detailed Description, when read in light of the attached drawings.

BRIEF DESCRIPTION OF THE DRAWINGS

FIG. 1 is an isometric view of a slide test element, such element featuring an ion-junction bridge that is either a prior art bridge or is constructed as per this invention;

FIG. 2 is an exploded isometric view of another test element, again featuring an ion-junction bridge that is either a prior-art bridge or constructed in accordance with the invention;

DETAILED DESCRIPTION OF THE PREFERRED EMBODIMENTS

Figure 3:
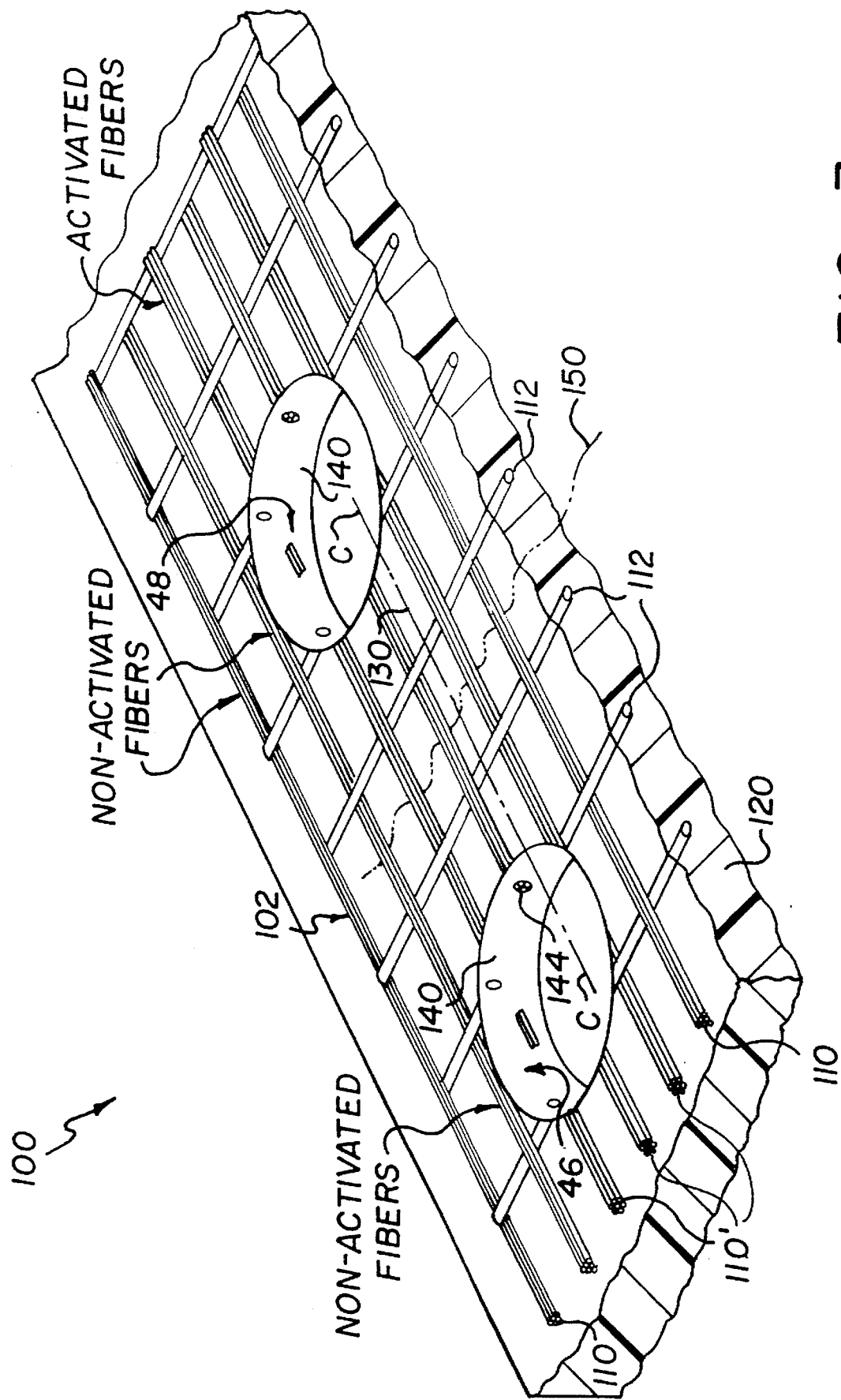
FIG. 3 is a fragmentary, partially schematic, isometric view of just an ion-junction bridge constructed in accordance with the invention, for use in the test element of either FIG. 1 or FIG. 2.

The invention is described hereinafter in connection with preferred slide test element constructions having a particular arrangement of electrodes, bridge, and a slide frame, and woven fibers of particular materials in the bridge. In addition, the invention is applicable regardless of the specific arrangement of parts of the slide test element, so long as the ion-junction bridge has two access apertures and at least one predominant aqueous flow direction that is generally aligned access apertures and at least one predominant aqueous flow direction that is generally aligned with the two apertures. As used herein, "generally aligned" means, along the center line drawn between the centers of the two apertures, plus or minus about 20°.

The invention is also useful whether or not the sheet of fibers of the bridge is woven with only two directions (warp and weft) and regardless of the materials selected to produce a predominant flow in a direction.

FIGS. 1 and 2 illustrate some typical preferred constructions for slide test elements. In test element 10, FIG. 1, two solid electrodes 12 and 14 are mounted on a frame 16, and a capillary bridge 18 is provided for promoting ionic migration between two fluid access holes 20 and 22 at the electrodes. The capillary bridge includes a nonporous support layer, a porous layer with ionic access to both electrodes, and a top nonporous cover layer which is preferably non-aqueous-conducting. When a drop of reference solution of known ion activity is applied to one fluid access hole and a drop of test solution is applied to the other fluid access hole, the drops spread into the porous layer until contact is made at a thin junction interface between the apertures, permitting ionic migration between the drops. An electrometer 24 is provided to measure the electrical potentials at the interfaces between each solution drop and its associated electrode to provide an indication of ion activity in the test solution.

In a similar manner, an alternative useful construction, FIG. 2, features a test element 30 solid electrodes 38 and 40 are mounted in the frame and electrically isolated from each other. A cover sheet 42, with an internal capillary ion bridge 44 embedded therein, promotes ionic migration between solution drops deposited in fluid access holes 46 and 48. The fluid access holes extend through the cover sheet in the region of, and to provide fluid contact with, electrodes 38 and 40. Two electrical access holes 50 and 52 are also formed in the cover sheet.

In both embodiments (of FIG. 1 and FIG. 2), the electrodes and their use are conventional and require no further discussion.

It will be readily appreciated that if the embodiment of FIG. 1 or FIG. 2 is constructed in accord with the prior art, the ion-junction bridge comprises a porous sheet of material, such as fibers, which allows flow generally in all directions. E.g. bridge 44, FIG. 2, is formed from paper such as the Whatman #2 chroma sheet described in the aforesaid U.S. Pat. No. 4,273,639. It is this kind of bridge that is improved upon by this invention.

THE INVENTION

In accordance with the invention, the ion-junction bridge in either the embodiment of FIG. 1 or FIG. 2 comprises bridge 100 shown in FIG. 3. More specifically, such a bridge comprises a sheet 102 of fibers, preferably a woven sheet in which the fibers extend in two orthogonal directions. The machine direction, or warp fibers, are those fibers 110 and 110', and the weft direction fibers are fibers 112 extending generally perpendicularly to fibers 110. As in most ion-junction bridges, liquid access apertures 46 and 48 extend all the way through sheet 102, to provide fluid contact with an ion-selective electrode located underneath (not shown). Optionally, but not necessarily, sheet 102 is embedded in a layer 120 of plastic, such as polystyrene or polyethylene.

Aperture 46 and 48 each has a side wall 140 which intersects fibers 110' and some of fibers 112. Stated in other words, apertures 46 and 48, when punched out of the bridge, have exposed at wall 140, ends or side portions of fibers 110' and 112. See for example, end 144 in the sidewall of aperture 46 of a fiber 110'. However, to provide mono-directional flow, only the thus-exposed portions of fibers 110' are capable of extensive absorption and carrying of the liquid deposited in the aperture, as will become apparent. (The illustration in FIG. 3 is schematic, because preferably there are more fibers per inch than shown—about 20 to 40 per inch, for example. Also, there may be more than one layer.)

Unlike fibers 110', fibers 110 are not active carriers of the liquid as they do not intersect wall 140.

Importantly, fibers 110 extend in a direction that is generally aligned with center line 130 extending between center-points C of apertures 46 and 48. That is, the lines along which the warp fibers 110 extend deviate from center-line 130 by an angle of no greater than about 20°, and most preferably, no greater than about 17° to ensure that liquid flow along fibers 110 intersects both apertures.

Also importantly, fibers 110,110' comprise an aqueous-conducting material, whereas fibers 112 comprise a non-aqueous-conducting material. As used herein, "aqueous-conducting" means, conducting aqueous liquid readily along the length of the fiber. Any suitable materials having these properties can be used. Preferred aqueous-conducting materials are selected from the group consisting of cotton, acetate, and rayon, multifilament or hollow core yarn, as well as hollow core yarn made from water-repellant materials such as polyester and polypropylene. The latter hollow core yarn are useful because the hollow core will conduct aqueous liquid through the core, notwithstanding that the shell around the core is water-repellant. Preferred non-aqueous-conducting materials are mono- or multifilament yarn selected from the group consisting of polyester, polypropylene, and any aqueous-conducting material coated with a water-repellent composition. Preferred water-repellent compositions are selected from the group consisting of wax, poly(tetrafluoroethylene), silicone, and fluourinated vinyl polymers such as "Scotchgard" ® polymer available from 3M Company. Thus, a highly preferred non-aqueous-conducting material is cotton yarn coated with "Scotchgard" ®, obtainable from 3M Company.

Thus it is that an aqueous liquid, e.g., a reference liquid or patient sample, when placed in either aperture 46 or 48, will traverse along primarily fibers 110', and not fibers 112, not even those fibers 112 that intersect a sidewall 140. An ion junction then forms somewhere between the two apertures, e.g. along wavefront 150, created when the two liquids meet along fibers 110'.

Figure 4:
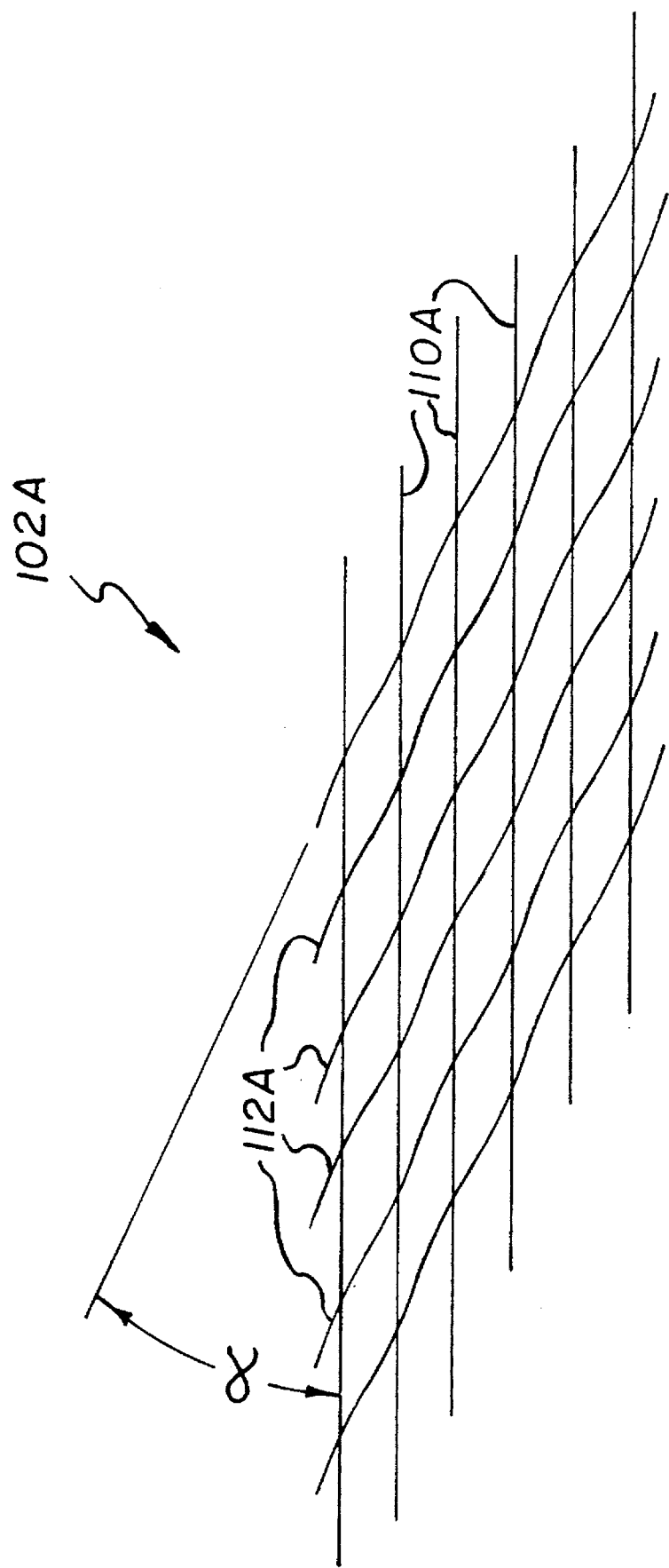
FIG. 4 is a fragmentary plan view of an alternative embodiment of the invention.

As shown in FIG. 4, it is not necessary for the invention that the fibers 112A in the weft direction, be almost perpendicular to fibers 110A in the warp direction. (Parts similar to those previously described bear the same reference numeral to which the suffix A has been appended.) Thus, fibrous sheet 102A has warp direction fibers 110A, and weft direction fibers 112A angled to fibers 110A by an angle alpha, which is at least about 20°. The fibers 112A are primarily non-carriers of aqueous liquid, due to their non-aqueous-conducting composition. However, if angle alpha is less than 20°, then there is no need to exclude the weft fibers from carrying liquid-indeed such weft fibers become generally indistinguishable from the warp direction fibers.

The bridge 100, or that made from sheet 102A, can be substituted as a separate piece into the test element of FIGS. 1 or 2, in place of the prior art bridge. In the case of the FIG. 2 embodiment, fibrous sheet 102 can be embedded directly in the cover sheet 42 without first embedding it in the plastic 120.

Figure 5:
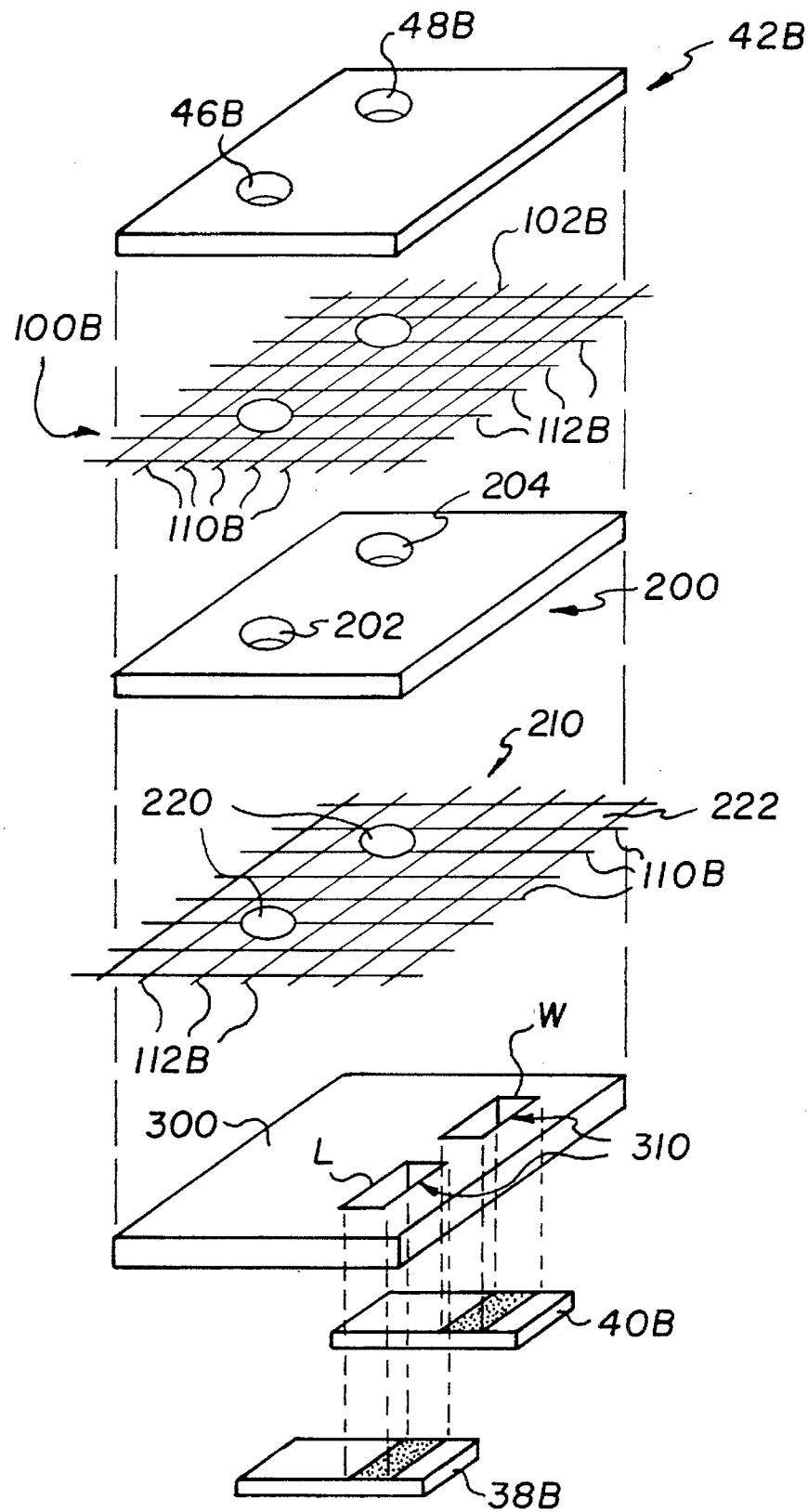
FIG. 5 is an exploded isometric view of an alternate embodiment of the invention.

It is not necessary that the ion bridge be the only item in the potentiometric test element that has a mono-directional flow property. FIG. 5 illustrates the manner in which a mono-directional flow can be expanded to include other, but separate, parts. Parts similar to those previously described bear the same reference numeral to which the suffix "B" is appended.

Thus, a cover sheet 42B has two liquid access apertures 46B, 48B, and an ion bridge 100B comprising a sheet 102B of fibers as described above. However, instead of the ISEs being disposed directly underneath sheet 102B (which may be embedded in plastic), there is interposed a new sheet of plastic 200 apertured at 202, 204. Below that is a second sheet 210 of fibers which comprises aqueous-conducting fibers 110B and non-aqueous-conducting fibers 112B, just as with bridge sheet 100B, except that fibers 110B of sheet 210 run substantially perpendicular to the direction of fibers 110B in sheet 100B. Also, unlike sheet 100B, sheet 210 should not be embedded in plastic since it needs to adequately wet the apertures in the plastic sheet below it, discussed below. The orientation of fibers 110B causes flow of liquid reaching sheet 210 to proceed away from contact points 220 of sheet 210 towards end 222 of sheet 210, that is, orthogonal to the direction of predominant flow in sheet 100B. End 222 overlies apertures 310 in the sheet of plastic 300 disposed below. It is apertures 310 which in turn conduct liquid flow down to the ISEs 38B, 40B that are mounted below sheet 300. To ensure liquid will "turn the corner" and flow from sheet 210 to the ISEs, apertures 310 are constructed with the properties explained in commonly-owned U.S. Pat. No. 4,271,119, the details of which are expressly incorporated herein. For example, the length L can be much greater than the width W of these apertures, as described in the '119 patent. Additionally, a filter paper material, such as Whatman filter paper, not shown, can be inserted into apertures 310 to aid in wetting the ISEs below.

As with sheet 100B, fibers 110B of sheet 210 can also deviate from the direction exactly orthogonal to the center line 130B between centers of contact 220, but by no more than about 20°.

The advantage of this construction is that the portion of the ISEs that is contacted with liquid (shown shaded) is no longer exposed to air. Such air exposure has been found to be detrimental in certain circumstances, and this embodiment avoids that.

Figure 6:
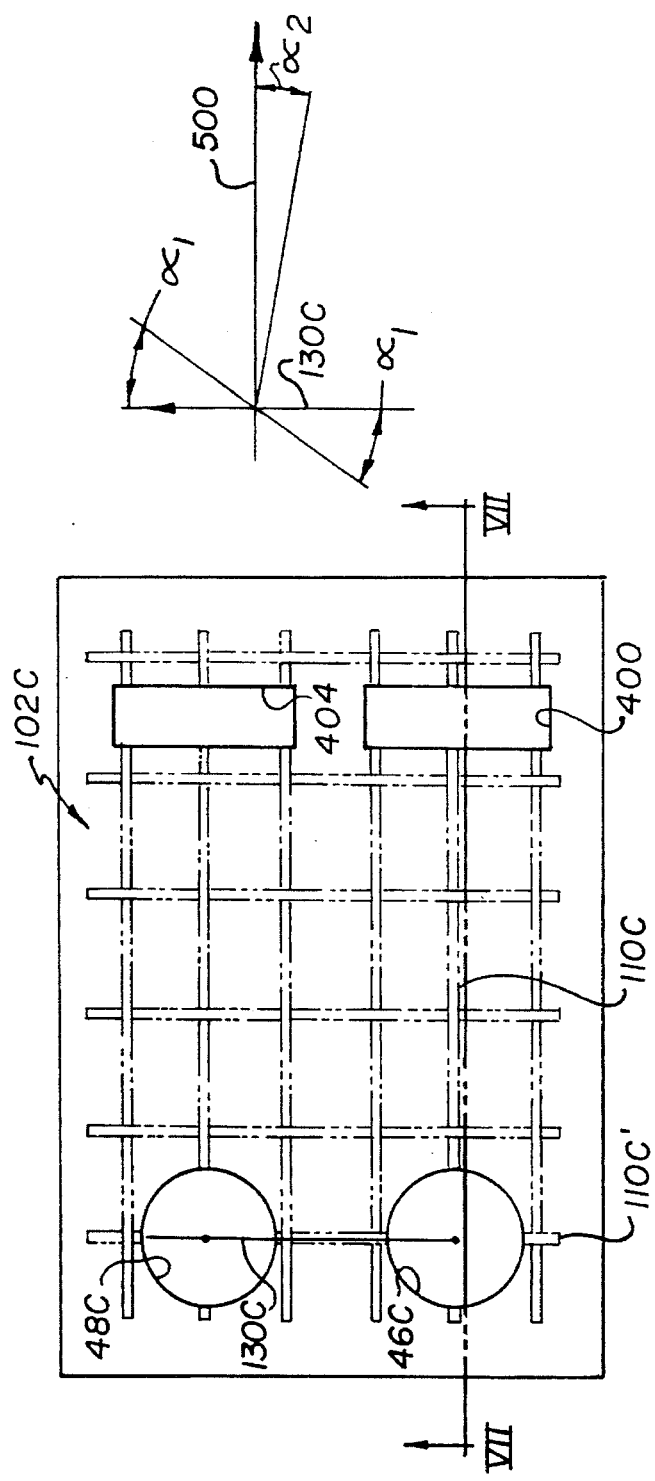
FIG. 6 is a partially schematic plan view of still another embodiment of the invention.
Figure 7:
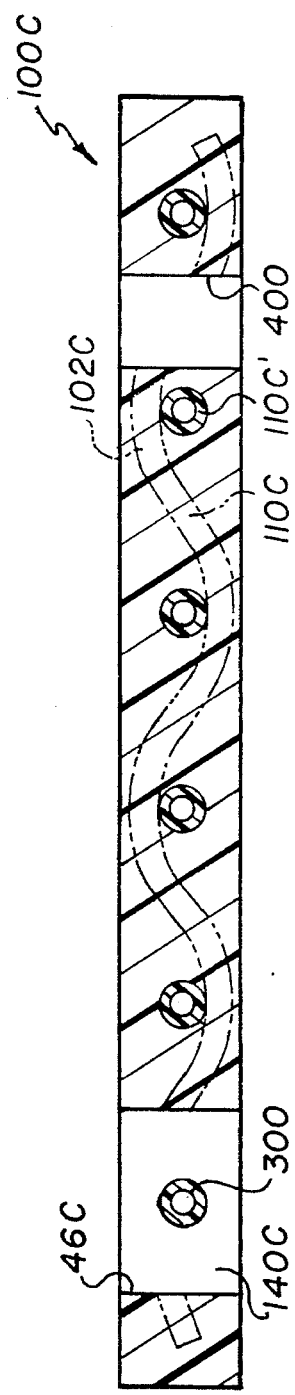
FIG. 7 is a section view taken generally along line VII—VII of FIG. 6, wherein the number of fibers shown is schematic for simplicity.

It is also not necessary that each sheet of fibers conducting the liquid, be only mono-directional. That is, sheets 210 and 102B can be combined into a single sheet, FIGS. 6 and 7. Parts similar to those previously described bear the same reference numeral to which the distinguishing suffix "C" is applied. Thus, a test element can be constructed as in the case of the embodiment of FIG. 5, except that sheets 200 and 210 are omitted, and sheet 100B is modified as follows: FIG. 6 illustrates an ion bridge 100C that also acts to provide aqueous liquid flow in a direction generally orthogonal to the centerline direction of line 130C, but suppresses the flow in any direction that is angled more than about 20° from said orthogonal directions. Thus, as used herein "generally orthogonal" means, orthogonal within plus or minus 10°.

Specifically, sheet 102C of bridge 100C, shown embedded in plastic, has only fibers 110C and 110C' (in actuality, more numerous than those shown), going in both orthogonal directions as both the warp (110C) and the weft (110C') of the sheet. (In FIG. 7, the embedded warp fiber 110C is shown in dotted line.) To ensure these both are aqueous-conducting, they both comprise hollow-core fibers with water-repellant (non-aqueous-conducting) shells. They still conduct aqueous liquid, but only if they intersect vertical sidewall 140C of either aperture 46C or 48C, such as at openings 300, FIG. 7. However, there is a suppression of any flow that departs by more than 20° from the direction of the orthogonally-oriented fibers 110C and 110C'. That is, fibers 110C' can be off the centerline 130C, FIG. 6, by an angle $\propto_1$ which can be up to about 20°, and the fibers 110C can extend in a direction that departs from the direction 500 that is orthogonal to fibers 110C', whatever direction that is, by an angle $\propto_2$, which can be up to about 20°.

To ensure that liquid conducted along fibers 110C from apertures 46C, 48C is in fact delivered to apertures 310 of sheet 300 below, apertures 400, 404 are formed in sheet 100C, producing sidewalls 410 that intersect the hollow cores of fibers 110C. Apertures 400, 404 are preferably substantially the same size and shape as the apertures 310 below them, and aligned with them.

It will be readily apparent that only the fibers 110C and 110C' that are intersected by aperture 46C or 48C will conduct the liquid.

By this construction, the bridge will conduct fluid flow in substantially only the two directions that are needed, thus reducing the volume of liquid that would be needed compared to a bridge that flows in all directions.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. In an ion-junction bridge for bringing two liquids together to make an ion-exchange junction, said bridge comprising a sheet of fibers having two apertures therethrough;

the improvement wherein said fibers comprise a material which favors aqueous flow in a predominant direction and suppresses aqueous flow in directions angled away from said direction by at least 20°, said predominant direction being generally aligned with said two apertures, so that aqueous liquids deposited in said apertures will flow primarily in said predominant direction between said apertures and not in said angled directions, said sheet of fibers further comprising woven fibers extending in two generally orthogonal directions, one of which is the warp direction and the other the weft direction, said warp direction fibers comprising a aqueous-conducting material and said weft direction fibers comprising a non-aqueous-conducting material.

2. An ion-junction bridge as defined in claim 1, wherein said warp direction fibers are selected from the group consisting of cotton, acetate, rayon, and polyester.

3. An ion-junction bridge as defined in claim 1, wherein said weft direction fibers are selected from the group consisting of polyester, polypropylene, and any aqueous-conducting material coated with a water-repellent composition.

4. An ion-junction bridge as defined in claim 3, wherein said water-repellent composition is selected from the group consisting of wax, poly (tetrafluoroethylene), silicone, and fluorinated vinyl polymers.

5. An ion-junction bridge as defined in claim 4, wherein said weft direction fibers comprise cotton coated with fluorinated vinyl polymers.

6. A potentiometric test element comprising a frame, two substantially identical ion-selective electrodes mounted, spaced apart on said frame, and an ion-junction bridge extending between said electrodes, said bridge comprising a sheet of fibers having two liquid access apertures through said sheet, each aperture being disposed above and in fluid contact with one of said electrodes, said fibers comprising a material which favors aqueous flow in a predominant direction and suppresses aqueous flow in directions angled away from said one direction by at least 20°, said predominant direction being generally aligned with said two apertures, so that aqueous liquids deposited in said apertures will flow primarily in said predominant direction between said apertures and not in said angled directions, said sheet of fibers further comprising woven fibers extending in two generally orthogonal directions, one of which is the warp direction and the other the weft direction, said warp direction fibers comprising a aqueous-conducting material and said weft direction fibers comprising a non-aqueous-conducting material.

7. A test element as defined in claim 6, wherein said warp direction fibers are selected from the group consisting of cotton, acetate, rayon, and polyester.

8. A test element as defined in claim 6, wherein said weft direction fibers are selected from the group consisting of polyester, polypropylene, and any aqueous-conducting material coated with a water-repellent composition.

9. A potentiometric test element comprising a frame, two substantially identical ion-selective electrodes mounted, spaced apart on said frame, and an ion-junction bridge extending between said electrodes, said bridge comprising a sheet of fibers having two liquid access apertures through said sheet, each aperture being disposed above and in fluid contact with one of said electrodes, said fibers comprising a material which favors aqueous flow in a predominant direction and suppresses aqueous flow in directions angled away from said one direction by at least 20°, said predominant direction being generally aligned with said two apertures, so that aqueous liquids deposited in said apertures will flow primarily in said predominant direction between said apertures and not in said angled directions, and further including a second sheet of fibers spaced away from said bridge sheet of fibers, said second sheet comprising a material which favors aqueous flow in a predominant direction and suppresses aqueous flow in directions angled away from said predominant direction by at least 20°, said predominant direction of said second sheet of fibers being generally orthogonal to said predominant direction of said bridge sheet of fibers.

10. A potentiometric test element comprising a frame, two substantially identical ion-selective electrodes mounted, spaced apart on said frame, and an ion-junction bridge extending between said electrodes, said bridge comprising a sheet of fibers having two liquid access apertures through said sheet, each aperture being disposed above and in fluid contact with one of said electrodes, said fibers comprising a material which favors aqueous flow in no more than two generally orthogonal directions and suppresses aqueous flow in directions angled away from either of said orthogonal directions by more than about 20°, one of said orthogonal directions being generally aligned with said two apertures, so that aqueous liquids deposited in said apertures will flow primarily in said orthogonal directions, said sheet of fibers further comprising a weave of hollow core fibers having a shell that is water-repellant, so that said fibers conduct liquid only if the core thereof is in fluid contact with said apertures.

* * * * *